United States Patent
Simon et al.

(10) Patent No.: US 10,668,005 B2
(45) Date of Patent: Jun. 2, 2020

(54) ORAL CARE COMPOSITIONS WITH INCREASED WHITENING EFFICACY

(71) Applicant: Colgate-Palmolive Company, New York, NY (US)

(72) Inventors: Eric Simon, Princeton, NJ (US); Venda Porter Maloney, Piscataway, NJ (US); Hallena Strotman, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/348,165

(22) PCT Filed: Nov. 8, 2016

(86) PCT No.: PCT/US2016/061008
§ 371 (c)(1),
(2) Date: May 8, 2019

(87) PCT Pub. No.: WO2018/088995
PCT Pub. Date: May 17, 2018

(65) Prior Publication Data
US 2019/0269601 A1    Sep. 5, 2019

(51) Int. Cl.
| A61K 8/81 | (2006.01) |
| A61K 8/21 | (2006.01) |
| A61K 8/46 | (2006.01) |
| A61Q 11/00 | (2006.01) |
| A61K 8/19 | (2006.01) |
| A61K 8/49 | (2006.01) |

(52) U.S. Cl.
CPC .............. *A61K 8/8152* (2013.01); *A61K 8/19* (2013.01); *A61K 8/21* (2013.01); *A61K 8/463* (2013.01); *A61K 8/466* (2013.01); *A61K 8/494* (2013.01); *A61Q 11/00* (2013.01); *A61K 2800/43* (2013.01); *A61K 2800/58* (2013.01)

(58) Field of Classification Search
CPC . A61K 8/46; A61K 11/00; A61K 8/22; A61K 8/24; C08L 43/00
USPC .......................................................... 424/57
See application file for complete search history.

(56) References Cited

U.S. PATENT DOCUMENTS

| 9,138,600 | B2 | 9/2015 | Batchelor |
| 9,808,412 | B2 | 11/2017 | Nesta et al. |
| 10,092,482 | B2 | 10/2018 | Maitra |
| 2006/0024246 | A1 | 2/2006 | Maitra |
| 2008/0152599 | A1 | 6/2008 | Brignoli et al. |
| 2016/0331663 | A1 | 11/2016 | Maloney |
| 2017/0266092 | A1 | 9/2017 | Maloney et al. |

FOREIGN PATENT DOCUMENTS

| EP | 1935395 | | 6/2008 | |
| RU | 2404739 | | 11/2010 | |
| WO | WO2015094332 | * | 6/2015 | ............... A61K 8/81 |
| WO | WO2015094333 | * | 6/2015 | ............. A61Q 11/00 |
| WO | WO2016099524 | * | 6/2016 | ............... A61K 6/46 |

OTHER PUBLICATIONS

International Search Report and Written Opinion of the International Searching Authority in International Application No. PCT/US2016/061008, dated Feb. 3, 2017.

* cited by examiner

*Primary Examiner* — Walter E Webb

(57) ABSTRACT

An oral care composition and method for whitening teeth is disclosed. The oral care composition includes an orally acceptable vehicle, a blue dye and/or blue pigment having a blue to blue-violet color with a hue angle in the CIELAB system from about 200 to about 320 degrees, and a phosphate/acrylate copolymer.

15 Claims, No Drawings

ORAL CARE COMPOSITIONS WITH INCREASED WHITENING EFFICACY

BACKGROUND

As is known in the art, the visual perception of a white substance can be altered through the deposition of a blue pigment and/or a blue dye. For example, blue dye and/or blue pigment added to oral care products may be deposited onto teeth, thereby allowing the off-white and/or yellow color of the teeth to appear whiter to the human eye.

While these oral care products provide effective whitening after only a single use, the blue dye and/or blue pigment may only remain deposited on the teeth for a limited duration, thereby allowing the yellow stains to eventually reappear. Additionally, increasing the relative concentration of the blue dye and/or the blue pigment does not increase the duration of deposition. Instead, the relatively higher concentrations may result in an increased deposition of the blue dye and/or blue pigment, which may make the teeth appear blue and/or stain soft tissues of the mouth. Accordingly, improved oral care compositions and methods for prolonged deposition of the blue dye and/or blue pigment are desired.

BRIEF SUMMARY

This summary is intended merely to introduce a simplified summary of some aspects of one or more embodiments of the present disclosure. Further areas of applicability of the present invention will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing an oral care composition, including an orally acceptable vehicle, an blue dye and/or blue pigment having a blue to blue-violet color with a hue angle in the CIELAB system from about 200 to about 320 degrees, and a phosphate/acrylate copolymer.

In another embodiment, the phosphate/acrylate copolymer is a copolymer of a mixture of acrylic acid, methacrylic acid, and 2-hydroxyethyl methacrylate phosphate.

In another embodiment, the mixture of acrylic acid, methacrylic acid, and 2-hydroxyethyl methacrylate phosphate includes the acrylic acid in a molar percentage of 70-90%, the methacrylic acid in a molar percentage of 5-20%, and the 2-hydroxyethyl methacrylate phosphates in a molar percentage of 1-10%.

In another embodiment, the acrylic acid is present in a molar percentage of about 80% to about 90%, optionally about 85%, the methacrylic acid is present in a molar percentage of about 5% to about 15%, optionally about 11%, and the 2-hydroxyethyl methacrylate phosphates is present in a molar percentage of about 2% to about 6%, optionally about 4%.

In another embodiment, the phosphate/acrylate copolymer has a weight average molecular weight of about 10 kDa to about 500 kDa, optionally about 10 kDa to about 200 kDa, further optionally about 10 kDa to about 40 kDa.

In another embodiment, the oral care composition includes about 0.70 wt % to about 2.20 wt %, optionally about 0.90 wt % to about 2.00 wt %, further optionally about 1.00 wt % to about 1.95 wt %, of the phosphate/acrylate copolymer.

In another embodiment, the phosphate/acrylate copolymer is a sodium salt of a sodium acrylates/methacryloylethyl phosphate copolymer.

In another embodiment, the oral care composition is a mouthwash.

In another embodiment, the oral care composition includes about 0.0010 wt % to about 0.0030 wt %, optionally about 0.0015 wt % to about 0.0025 wt %, further optionally about 0.002 wt % of the blue dye and/or blue pigment.

In another embodiment, the blue dye and/or blue pigment includes a dye, optionally the dye comprises FD&C Blue No. 1.

In another embodiment, the oral care composition further includes a fluoride ion source, optionally the fluoride ion source includes sodium fluoride.

In another embodiment, the oral care composition further includes an antibacterial agent.

In another embodiment, the oral care composition is free of peroxides.

In another embodiment, the oral care composition further includes at least one anionic surfactant and at least one nonionic surfactant, optionally the anionic surfactant includes sodium lauryl sulfate.

The foregoing and/or other aspects and utilities embodied in the present disclosure may also be achieved by providing a method for whitening teeth, including contacting an oral care composition with a surface of the teeth, where the oral care composition includes an orally acceptable vehicle, an blue dye and/or blue pigment having a blue to blue-violet color with a hue angle in the CIELAB system from about 200 to about 320 degrees, and a phosphate/acrylate copolymer.

Further areas of applicability of the present invention will become apparent from the detailed description provided hereinafter. It should be understood that the detailed description and specific examples, while indicating some preferred aspects of the invention, are intended for purposes of illustration only and are not intended to limit the scope of the invention.

DETAILED DESCRIPTION

The following description of various preferred aspect(s) is merely exemplary in nature and is in no way intended to limit the invention, its application, or uses.

As used throughout, ranges are used as shorthand for describing each and every value that is within the range. Any value within the range may be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith.

Compositions

The present inventors have surprisingly and unexpectedly discovered that oral care compositions including a blue dye and/or blue pigment and a phosphate/acrylate copolymer enhance whitening efficacy of teeth. The present inventors have also surprisingly and unexpectedly discovered that oral care products, or the oral care compositions thereof, including a blue dye and/or blue pigment and a phosphate/acrylate copolymer, when combined with one another, exhibit a synergistic effect and provide a significant and unexpected increase in whitening efficacy over conventional oral care products or conventional oral care compositions thereof without the phosphate/acrylate copolymer.

Without being bound by theory, it is believed that the phosphate/acrylate copolymer may prolong the duration in which the blue dye and/or blue pigment may be deposited on the teeth by facilitating or enhancing the deposition of blue dye and/or blue pigment on the teeth. For example, the phosphate/acrylate copolymer may facilitate the deposition of the blue dye and/or blue pigment on surfaces of the teeth. Accordingly, the oral care compositions disclosed herein may have relatively greater or enhanced whitening efficacy and/or duration as compared to the conventional oral care compositions that include the blue dye and/or blue pigment without the phosphate/acrylate copolymer. The oral care compositions disclosed herein may also have relatively greater or enhanced whitening efficacy and/or duration as compared to conventional or commercially available oral care compositions that include an blue dye and/or blue pigment and a synthetic anionic linear polycarboxylate, such as GANTREZ® S-97 Pharmaceutical Grade, available from Ashland Specialty Chemicals, Bound Brook, N.J. 08805. Additionally, in view of the enhanced whitening efficacy and/or duration, the oral care compositions, and the oral care products incorporating the oral care compositions, may include reduced amounts of the blue dye and/or blue pigment without a concomitant decrease in whitening efficacy. As further described herein, the oral care compositions may form at least a portion of or be used in one or more oral care products (e.g., mouthwash).

Phosphate/Acrylate Copolymer

As used herein, "phosphate/acrylate copolymer" may refer to a polymer made up of acrylate monomers and phosphate-bearing monomers. The phosphate/acrylate copolymer may be or include a copolymerized product of a mixture of acrylic acid, methacrylic acid, and 2-hydroxyethyl methacrylate phosphates. In at least one embodiment, the 2-hydroxyethyl methacrylate phosphate may be represented by Formula (1):

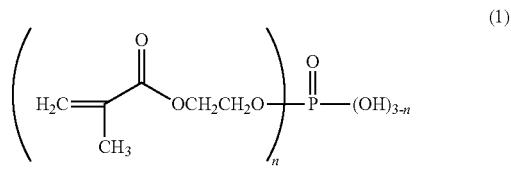

wherein n is 0, 1 or 2. In some embodiments, the phosphate/acrylate copolymer may be a copolymerized product of a mixture of acrylic acid, methacrylic acid, and 2-hydroxyethyl methacrylate phosphates of Formula (1), where the acrylic acid is in a molar percentage or molar proportion (mol %) of about 70-90%, 80-90%, or about 85%; the methacrylic acid is in a molar percentage of about 5-20%, 5-15%, or about 11%; and the 2-hydroxyethyl methacrylate phosphates of Formula (1) is in a molar percentage of about 1-10%, 2-6%, or about 4%. The phosphate/acrylate copolymer may have a weight average molecular weight of from about 10 to about 500 kDa, about 10 kDa to about 200 kDa, about 10 kDa to about 40 kDa, about 15 kDa to about 25 kDa, or about 17 kDa to about 23 kDa. The phosphate/acrylate copolymer may be below its glass transition temperature.

In a preferred embodiment, the phosphate/acrylate copolymer has a weight average molecular weight of about 17 kDa to about 23 kDa. In another preferred embodiment, the phosphate/acrylate copolymer includes DV8801 (Rhodia). In at least one embodiment, the phosphate/acrylate copolymer is the sodium salt of a copolymer of acrylic acid, methacrylic acid, or one or more of its simple esters, and methacryloylethyl phosphates. In an exemplary embodiment, the phosphate/acrylate copolymer is the copolymerized product of a mixture of 2-hydroxyethy methacrylate phosphates, acrylic acid, and methacrylic acid, in the relative amounts set forth in Table 1 below.

TABLE 1

| Monomer Name and Structure | Monomer Weight Ratio (weight %) | Monomer Molar Ratio (Mole %) |
|---|---|---|
| 2-hydroxyethyl methacylate phosphates | 11 | 4 |
| mixture of n = 0, n = 1, and n = 2 | | |
| acrylic add | 75 | 85 |

TABLE 1-continued

| Monomer Name and Structure | Monomer Weight Ratio (weight %) | Monomer Molar Ratio (Mole %) |
|---|---|---|
| methacrylic acid 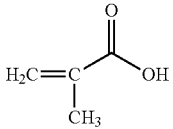 | 14 | 11 |

The amount of the phosphate/acrylate copolymer included in the oral care composition may widely vary. For example, the amount of the phosphate/acrylate copolymer in the oral care composition may be from about 0.50 wt %, about 0.60 wt %, about 0.70 wt %, about 0.80 wt %, about 0.90 wt %, about 1.00 wt %, about 1.10 wt %, about 1.20 wt %, about 1.30 wt %, about 1.35 wt %, about 1.40 wt %, about 1.45 wt %, about 1.48 wt %, or about 1.49 wt % to about 1.51 wt %, about 1.52 wt %, about 1.50 wt %, about 1.55 wt %, about 1.60 wt %, about 1.65 wt %, about 1.70 wt %, about 1.75 wt %, about 1.80 wt %, about 1.85 wt %, about 1.90 wt %, about 1.95 wt %, or greater. In another example, the amount of the phosphate/acrylate copolymer in the oral care composition may be about 0.50 wt % to about 2.40 wt %, about 0.60 wt % to about 2.30 wt %, about 0.70 wt % to about 2.20 wt %, about 0.80 wt % to about 2.10 wt %, about 0.90 wt % to about 2.00 wt %, about 1.00 wt % to about 1.95 wt %, about 1.10 wt % to about 1.85 wt %, about 1.20 wt % to about 1.75 wt %, about 1.30 wt % to about 1.65 wt %, about 1.35 wt % to about 1.60 wt %, about 1.40 wt % to about 1.55 wt %, about 1.45 wt % to about 1.55 wt %, about 1.48 wt % to about 1.52 wt %, or about 1.49 wt % to about 1.51 wt %. In another example, the amount of the phosphate/acrylate copolymer in the oral care composition may be from about 0.65 wt %, about 0.75 wt %, about 0.85 wt %, about 0.95 wt %, about 1.05 wt %, about 1.15 wt %, about 1.25 wt %, about 1.35 wt %, or about 1.45 wt % to about 1.55 wt %, about 1.65 wt %, about 1.75 wt %, about 1.85 wt %, about 2.00 wt %, about 2.125 wt %, about 2.15 wt %, about 2.175 wt %, about 2.25 wt %, or greater. In another example, the amount of the phosphate/acrylate copolymer in the oral care composition may be less than 2.25 wt %, less than 2.20 wt %, less than 2.18 wt %, less than 2.16 wt %, less than 2.14 wt %, less than 2.12 wt %, less than 1.65 wt %, less than 1.60 wt %, less than 1.55 wt %, less than 1.50 wt %, or less than 1.45 wt %. In a preferred embodiment, the amount of the phosphate/acrylate copolymer in the oral care composition may be about 1.50 wt %.

Blue Dye and/or Blue Pigment

The oral care composition may include one or more blue dye and/or blue pigment. The blue dye and/or the blue pigment may be a substance in the form of a solid (e.g., a dry powder) or a fluid (e.g., a liquid) that imparts color to another substance or substrate.

The amount of any one or more of the blue dye and/or blue pigment included in the oral care composition may widely vary. For example, the amount of any one or more of the blue dye and/or blue pigment in the oral care composition may be from about 0.0006 wt %, about 0.0007 wt %, about 0.0008 wt %, about 0.0009 wt %, about 0.0010 wt %, about 0.0011 wt %, about 0.0012 wt %, about 0.0013 wt %, about 0.0014 wt %, about 0.0015 wt %, about 0.0016 wt %, about 0.0017 wt %, about 0.0018 wt %, or about 0.0019 wt % to about 0.0021 wt %, about 0.0022 wt %, about 0.0023 wt %, about 0.0024 wt %, about 0.0025 wt %, about 0.0026 wt %, about 0.0027 wt %, about 0.0028 wt %, about 0.0029 wt %, about 0.0030 wt %, about 0.0031 wt %, about 0.0032 wt %, or greater. In another example, the amount of any one or more of the blue dye and/or blue pigment in the oral care composition may be about 0.0001 wt % to about 0.0040 wt %, about 0.0005 wt % to about 0.0035 wt %, about 0.0010 wt % to about 0.0030 wt %, about 0.0015 wt % to about 0.0025 wt %, about 0.0016 wt % to about 0.0024 wt %, about 0.0017 wt % to about 0.0023 wt %, about 0.0018 wt % to about 0.0022 wt %, or about 0.0019 wt % to about 0.0021 wt %. In at least one embodiment, the amount of any one or more of the blue dye and/or blue pigment in the oral care composition may be about 0.00200 wt % or about 0.0014 wt %. In another example, the amount of any one or more of the blue dye and/or blue pigment in the oral care composition may be about 0.0010 wt % to about 0.0090 wt %, about 0.0020 wt % to about 0.0080 wt %, about 0.0030 wt % to about 0.0070 wt %, or about 0.0040 wt % to about 0.0060 wt %. In another example, the amount of any one or more of the blue dye and/or blue pigment in the oral care composition may be about 0.00001 wt % to about 0.00015 wt %, about 0.00002 wt % to about 0.00014 wt %, about 0.00003 wt % to about 0.00013 wt %, about 0.00004 wt % to about 0.00012 wt %, about 0.00005 wt % to about 0.00011 wt %, about 0.00006 wt % to about 0.00010 wt %, or about 0.00007 wt % to about 0.00009 wt %. In another example, a total amount of all the blue dye and/or blue pigment in the oral care composition may be about 0.0012 wt % to about 0.0022 wt %, about 0.0014 wt % to about 0.0020 wt %, about 0.0020 wt % to about 0.0100 wt %, about 0.0030 wt % to about 0.0090 wt %, about 0.0040 wt % to about 0.0080 wt %, about 0.0055 wt % to about 0.0075 wt %, or about 0.0060 to about 0.0070 wt %. For example, a total amount of the blue dye and/or blue pigment included in the oral care composition may be about 0.0065 wt %. It should be appreciated that the amount of any one or more of the blue dye and/or blue pigment contained in the oral care composition may at least partially depend upon the type of the blue dye and/or blue pigment used. For example, as further described in Example 1, 0.0014 wt % of CI Food Blue 5 is substantially equivalent to 0.002 wt % of FD&C Blue No. 1.

Pigments

As previously discussed, the oral care composition may include one or more pigments. As used herein, the term "pigment" may refer to a synthetic or natural water insoluble substance, which imparts color to another substance. The one or more pigments may be configured to enhance the whiteness of the teeth. For example, the pigments may be deposited on a surface of the teeth to alter the visually perceived whiteness of the teeth.

The one or more pigments may have a hue angle, in the CIELAB scale, of from about 200 degrees to about 320 degrees. For example, the pigments may have a hue angle between about 250 and about 290 degrees. It should be appreciated that "CIELAB" is a color measurement system or standard adopted by the Commission Internationale de l'Eclairage (CIE) in 1976. It is based on a three-dimensional CIELAB color space. The system was developed to represent color in a manner that is consistent with human vision and proportional to perceived color differences. CIELAB values describe coordinates of a specific color in the three dimensional CIELAB color space. There are three axes: L* (defining light to dark); b* (defining blue to yellow); and a* (defining red to green). Any point in the three dimensional CIELAB color space may be defined by its L*, a*, and b* coordinates. The same point may also be defined by L*, hue angle, and chroma, which uses cylindrical coordinates. The hue angle is defined by the formula: $H_{ab} = \tan^{-1}(b^*/a^*)$, where a* and b* are coordinates in the L*a*b* three dimensional CIELAB color space. A detailed description of hue angle may be found in M. L. Gulrajani (Ed.), (2010). *Colour Measurement. Principles, Advances and Industrial Applications*. Cambridge, United Kingdom: Woodhouse Publishing, which is herein incorporated by reference in its entirety.

The one or more pigments of the oral care composition may be capable of reflecting sufficient light such that the treated teeth are perceivably whiter than their initial color. In some embodiments, the pigments may be colored such that its natural color is within the violet-red to green-blue color. More particularly, the pigment may be violet or blue (e.g., one of those listed in the Colour Index International). These pigments are listed as pigment violet 1 through to pigment violet 56 and pigment blue 1 through 83. In some embodiments, the pigment violets may be pigment violet 1, 1:1, 1:2, 2, 3, 5:1, 13, 19, 23, 25, 27, 31, 32, 37, 39, 42, 44, and 50. In some embodiments, the pigment blues may be pigment blue 1, 2, 9, 10, 14, 15, 15:1, 15:2, 15:3, 15:4, 15:6 16, 18, 19, 24:1, 25, 56, 60, 61, 62, and 66. Other suitable pigments may include, but are not limited to, pigment ultramarine blue and ultramarine violet. In an exemplary embodiment, the pigment is Pigment Blue 15, more typically the pigment is Pigment Blue 15:1, 15:2, 15:3, 15:4, 15:5 or 15:6, most typically 15:1.

While blue or violet single pigments may be used in the oral care composition, the same effect may be achieved through mixing pigments outside of the hue angle range of about 200 degrees to about 320 degrees. The desired hue angle may instead be obtained by mixing red and green-blue pigments to yield a blue or violet shaded pigment.

The amount of one or more of the pigments in the oral care composition may widely vary. For example, the amount of one or more of the pigments in the oral care composition may be from about 0.0006 wt %, about 0.0007 wt %, about 0.0008 wt %, about 0.0009 wt %, about 0.0010 wt %, about 0.0011 wt %, about 0.0012 wt %, about 0.0013 wt %, about 0.0014 wt %, about 0.0015 wt %, about 0.0016 wt %, about 0.0017 wt %, about 0.0018 wt %, or about 0.0019 wt % to about 0.0020 wt %, about 0.0025 wt %, about 0.0030 wt %, about 0.0035 wt %, about 0.0040 wt %, about 0.0045 wt %, about 0.0050 wt %, about 0.0055 wt %, about 0.0060 wt %, about 0.0065 wt %, about 0.0070 wt %, about 0.0080 wt %, or greater. In another example, the amount of one or more of the pigments in the oral care composition may be about 0.0006 wt % to about 0.0022 wt %, about 0.0007 wt % to about 0.0021 wt %, about 0.0008 wt % to about 0.0020 wt %, about 0.0009 wt % to about 0.0019 wt %, about 0.0010 wt % to about 0.0018 wt %, about 0.0011 wt % to about 0.0017 wt %, about 0.0012 wt % to about 0.0016 wt %, or about 0.0013 wt % to about 0.0015 wt %. In another example, the amount of one or more of the pigments in the oral care composition may be about 0.0010 wt % to about 0.0090 wt %, about 0.0020 wt % to about 0.0080 wt %, about 0.0030 wt % to about 0.0070 wt %, or about 0.0040 wt % to about 0.0060 wt %. In another example, the amount of one or more of the pigments in the oral care composition may be about 0.00001 wt % to about 0.00015 wt %, about 0.00002 wt % to about 0.00014 wt %, about 0.00003 wt % to about 0.00013 wt %, about 0.00004 wt % to about 0.00012 wt %, about 0.00005 wt % to about 0.00011 wt %, about 0.00006 wt % to about 0.00010 wt %, or about 0.00007 wt % to about 0.00009 wt %. In an exemplary embodiment, the oral care composition is free or substantially free of pigments. For example, the oral care composition may include only dyes.

In at least one embodiment, the one or more pigments may be disposed or dispersed uniformly throughout the oral care composition. In another embodiment, the one or more pigments may be disposed or dispersed in different phases of the oral care composition. For example, one or more of the pigments may be disposed or dispersed in a first phase (e.g., a hydrophobic phase) of the oral care composition, and one or more of the remaining pigments, or no pigment, may be disposed or dispersed in a second phase (e.g., a hydrophilic phase) of the oral care composition.

Dyes

As previously discussed, the oral care composition may include one or more dyes. The dyes may include any organic species that is substantially or essentially water soluble in an aqueous solution or medium in which the dye remains chemically stable. It should be appreciated, however, that some dyes may be soluble in an oil or hydrophobic phase. The one or more dyes may be configured to enhance the whiteness of the teeth. For example, the dyes may be deposited on the surface of the teeth to alter the visually perceived whiteness thereof. The dyes may generally be capable of reflecting sufficient light such that the treated teeth are perceivably whiter than its initial color (e.g., via spectrophotometric methods). Preferably, the one or more dyes are colored such that its natural color is within the violet-red to green-blue color, more preferably from a violet color to a blue color.

The one or more dyes may have a hue angle, in the CIELAB scale, of from about 200 degrees to about 320 degrees. For example, at least one of the dyes may have a hue angle of from about 200 to about 320 degrees. In another example, the one or more dyes may be contacted, mixed, or otherwise combined with one another to yield a hue angle of from about 200 to about 320 degrees. In an exemplary embodiment, the dyes may have a hue angle between about 250 and about 290 degrees.

In a preferred embodiment, one or more of the dyes are water soluble. As used herein, the term "water-soluble dye" may refer to dyes having an aqueous solubility of at least 10 g/L at 25° C., more preferably at least 100 g/L at 25° C., where the solubility is determined in un-buffered distilled water. The dyes may be or include, but are not limited to, triarylmethane dyes, especially anionic triphenylmethane dyes, such as diaminotriphenylmethane dyes containing from two to four sulphonate groups. A detailed description of triarylmethane dyes may be found in PCT Publication No. WO 2015/095709 to Colgate-Palmolive Company, which is herein incorporated by reference in its entirety.

The dyes may include any food color additives presently certified under the Food Drug & Cosmetic Act for use in food and ingested drugs. Illustrative dyes may include, but are not limited to, FD&C Blue No. 1 (Color Index [CI] 42090; CAS No. 3844-45-9), FD&C Blue No. 2 (CI 73015; CAS No. 860-22-0), CI Food Blue 5 or Acid Blue 3 (CI 42051; CAS No. 3536-49-0), Acid Blue 9 (CI 42090; CAS No. 2650-18-2), Acid Blue 1 (CI 42045; CAS No. 129-17-9), D&C Green No. 6 (CI 61565; CAS No. 128-80-3), D&C Violet No. 2 (CI 60725; CAS No. 81-48-1), D&C Green No. 5 (CI 61570; CAS No. 4403-90-1), D&C Orange No. 5 (CI 45370; CAS No. 596-03-2), D&C Red No. 21 (CI 45380; CAS No. 15086-94-9), D&C Red No. 22 (CI 45380; CAS No. 548-26-5), D&C Red No. 27 (CI 45410; CAS No. 13473-26-2), D&C Red No. 28 (CI 45410; CAS No. 18472-87-2), D&C Red No. 30 (CI 73360; CAS No. 2379-74-0), D&C Red No. 40 (CI 16035; CAS No. 25956-17-6), D&C Yellow No. 10 (CI 47005; CAS No. 68814-04-0), FD&C Yellow No. 5 (CI 19140; CAS No. 1934-21-0), FD&C Yellow No. 6 (CI 15985; CAS No. 2783-94-0), FD&C Green No. 3 (CI 42053; CAS No. 2353-45-9), FD&C Red No. 3 (CI 45430; CAS No. 16423-68-0), or the like, and combinations or mixtures thereof in varying proportions. In a preferred embodiment, the blue dye and/or blue pigment in the oral care composition may include the dye, FD&C Blue No. 1 (Color Index [CI] 42090; CAS No. 3844-45-9).

The amount of one or more of the dyes in the oral care composition may widely vary. For example, the amount of one or more of the dyes in the oral care composition may be from about 0006 wt %, about 0.0007 wt %, about 0.0008 wt %, about 0.0009 wt %, about 0.0010 wt %, about 0.0011 wt %, about 0.0012 wt %, about 0.0013 wt %, about 0.0014 wt %, about 0.0015 wt %, about 0.0016 wt %, about 0.0017 wt %, about 0.0018 wt %, or about 0.0019 wt % to about 0.0021 wt %, about 0.0022 wt %, about 0.0023 wt %, about 0.0024 wt %, about 0.0025 wt %, about 0.0026 wt %, about 0.0027 wt %, about 0.0028 wt %, about 0.0029 wt %, about 0.0030 wt %, about 0.0031 wt %, about 0.0032 wt %, or greater. In another example, the amount of one or more of the dyes in the oral care composition may be about 0.0001 wt % to about 0.0040 wt %, about 0.0005 wt % to about 0.0035 wt %, about 0.0010 wt % to about 0.0030 wt %, about 0.0015 wt % to about 0.0025 wt %, about 0.0016 wt % to about 0.0024 wt %, about 0.0017 wt % to about 0.0023 wt %, about 0.0018 wt % to about 0.0022 wt %, or about 0.0019 wt % to about 0.0021 wt %. In a preferred embodiment, the amount of any one or more of the blue dye and/or blue pigment in the oral care composition may be about 0.00200 wt %. In another example, the amount of one or more of the dyes in the oral care composition may be about 0.0010 wt % to about 0.0090 wt %, about 0.0020 wt % to about 0.0080 wt %, about 0.0030 wt % to about 0.0070 wt %, or about 0.0040 wt % to about 0.0060 wt %. In another example, the amount of one or more of the dyes in the oral care composition may be about 0.00001 wt % to about 0.00015 wt %, about 0.00002 wt % to about 0.00014 wt %, about 0.00003 wt % to about 0.00013 wt %, about 0.00004 wt % to about 0.00012 wt %, about 0.00005 wt % to about 0.00011 wt %, about 0.00006 wt % to about 0.00010 wt %, or about 0.00007 wt % to about 0.00009 wt %.

In at least one embodiment, the one or more dyes may be disposed or dispersed uniformly throughout the oral care composition. In another embodiment, the one or more dyes may be disposed or dispersed in different phases of the oral care composition. For example, one or more of the dyes may be disposed or dispersed in a first phase (e.g., a hydrophobic phase) of the oral care composition, and one or more of the remaining dyes, or no dye, may be disposed or dispersed in a second phase (e.g., a hydrophilic phase) of the oral care composition.

Whitening Efficacy

In some embodiments, the oral care composition disclosed herein has a whitening efficacy relatively greater than the whitening efficacy of a comparative or conventional oral care composition, which may include the same ingredients as the oral care composition of the present disclosure, except that the comparative composition does not contain the phosphate/acrylate copolymer. The oral care compositions disclosed herein may also have relatively greater or enhanced whitening efficacy and/or duration as compared to conventional or commercially available oral care compositions that include an blue dye and/or blue pigment and a synthetic anionic linear polycarboxylate, such as GANTREZ® S-97 Pharmaceutical Grade, available from Ashland Specialty Chemicals, Bound Brook, N.J. 08805. As used herein, the phrase "whitening efficacy" is intended to refer to the amount of change in tooth color. The color change may be measured according to the L*a*b* color scale. The luminance or lightness (L*) value measures brightness and varies from a value of one hundred for perfect white to zero for black, assuming a* and b* are zero. The a* value is a measure of redness when positive, gray when zero and greenness when negative. The b* value is a measure of yellowness when positive, gray when zero and blueness when negative. Generally, teeth appear whiter as: the L* value increases meaning they become brighter, the a* value increases or decreases, depending upon whether the stained teeth have a green tint or red tint prior to whitening, and the b* value decreases meaning they become less yellow. While this is the general relationship for perceived whitening, the b* value might also slightly increase if the magnitude of the increase of the L* value is large enough. Similarly, the L* value might also decrease if the magnitude of the decrease of the b* value is large enough to overshadow the less significant change in L*.

In some embodiments, a whitening index (WIO) is used to assess tooth whiteness. The whiteness index is based on the distance of a color value from a nominal white point, represented in the CIELAB colour space as L*=100, a*=0 and b*=0. Changes in the whitening index may be used to assess the whitening efficacy (ΔWIO) of a composition before and after a treatment. The whitening efficacy (ΔWIO) may be calculated according to formula (2), as described in Joiner et al., "A Review of Tooth Colour and Whiteness", *Journal of Dentistry*, 2008, 36S:S2-S7, the disclosure of which is incorporated herein by reference in its entirety.

$$\Delta WIO = WIO(\text{Treatment}) - WIO(\text{baseline}) \qquad (2)$$

Whitening efficacy of a composition may be determined by any method known in the art. For example, human teeth may be rinsed in water and brushed before baseline color measurements are made (using, for example, a Minolta chromameter CR300). The brushing may be performed using a brushing machine. The brushed teeth may then be soaked in sterile human saliva for 15 minutes, and then treated with (i) a composition of the present disclosure or (ii) a comparative composition. After treatment, the teeth may be rinsed with about 100 mL of water, and the color of the teeth may then be re-measured. The change in L*, a*, and b* may be recorded for both treatment (i) and treatment (ii) and the WIO and ΔWIO values calculated. From a comparison of these data, any whitening efficiency of a composition is readily seen. Other methods for assessing whitening efficacy are described in the Examples, herein below.

Whitening Agents

As used herein, a "whitening agent" may refer to a substance or material that effects whitening to the surfaces of teeth to which it is applied. Illustrative whitening agents may include, but are not limited to oxidizing agents, reducing agents, or combinations thereof. For example, whitening agents may include peroxides and bleaching ingredients. In at least one embodiment, the oral care composition disclosed herein may not include any, or may be free of, one or more whitening agent, such as the peroxides or peroxide compounds and/or the bleaching ingredients. In a preferred embodiment, the oral care composition disclosed herein may be free or substantially free of all of the whitening agents. Bleaching ingredients may include chlorites, and hypochlorites. Examples of chlorites and hypochlorites include those having alkali or alkaline metal cations, such as, calcium chlorite, barium chlorite, magnesium chlorite, lithium chlorite, sodium chlorite, potassium chlorite, calcium hypochlorite, barium hypochlorite, magnesium hypochlorite, lithium hypochlorite, lithium hypochlorite, and sodium hypochlorite.

The "peroxide" or "peroxide compound" may be an oxidizing compound comprising a bivalent oxygen-oxygen group. Peroxide compounds include peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, monoperoxyphthalate and mixtures thereof. Peroxy acids and their salts include organic peroxy acids such as alkyl peroxy acids, and monoperoxyphthalate, and mixtures thereof, as well as inorganic peroxy acid salts such as persulfate, dipersulfate, percarbonate, perphosphate, perborate, and persilicate salts of alkali and alkaline earth metals such as lithium, potassium, sodium, magnesium, calcium, and barium, and mixtures thereof. The peroxide compound may include hydrogen peroxide, urea peroxide, sodium percarbonate or mixtures thereof.

As used herein, the term "reducing agent" may refer to compounds that may donate an electron to another molecule in the environment of the oral cavity without having a deleterious or unacceptably harmful affect on the oral cavity in normal and accepted use. Synonyms for this term are preservatives, anti-oxidizing agents, or antioxidants. There are numerous compounds which have been proven to be useful as reducing agents. A list of such compounds currently recognized for this purpose may be found in reference manuals and compendia covering pharmaceutical and oral care products. Illustrative reducing agents may include, but are not limited to, vitamin C and its esters, citric acid, vitamin E, the benzoates and hydroxybenzoates, butylated hydroxytoluene (BHT), butylated hydroxyanisole (BHA) and other reducing phenols, derivatives of dihydroxyquinoline, derivatives of polymerized 2,2,4-trimethyl-1,2-dihydroquinoline and alkyl gallate such as dodecyl gallate, ethyl gallate, octyl gallate, and propyl gallate. In some embodiments, vitamin C, vitamin E, BHA, BHT, propyl gallate, and combinations thereof are used in the oral care composition.

As discussed above, in a preferred embodiment, the oral care composition may be free or substantially free of one or more of the whitening agents, such as the peroxides or peroxide compounds and/or the bleaching ingredients. As used herein, the terms "free" or "substantially free" may refer to a composition that contains less than 0.1 wt %, less than 0.05 wt %, less than 0.01 wt %, less than 0.005 wt %, or less than 0.0001 wt %. Accordingly, the tooth whitening effect of the oral care composition may be provided by the blue dye and/or blue pigment rather than by the presence of any whitening agents. For example, the tooth whitening effect of the oral care composition may be provided by the presence of a phosphate/acrylate copolymer in combination with the dye and/or the pigments, rather than by the presence of any peroxide whitening agents.

Vehicle

The oral care composition may form at least a portion of or be used in one or more oral care products. Illustrative oral care products may include, but are not limited to, a toothpaste (dentifrice), a prophylactic paste, a tooth powder, a tooth polish, a tooth gel, a chewing gum, a lozenge, a mouthwash, a whitening strip, a paint-on gel, varnish, veneer, and tube, syringe or dental tray comprising a gel or paste, or a gel or paste coated on an application support such as dental floss or a toothbrush (e.g., a manual, electric, sound, a combination thereof or ultrasound toothbrush). In an exemplary embodiment, the oral care composition may form at least a portion of or be used in a mouthwash. For example, the oral care composition may include or be combined with an orally acceptable vehicle to form the oral care product (e.g., the mouthwash). In at least one embodiment, the oral care composition may be combined with an orally acceptable vehicle including a hydrophilic phase and a hydrophobic phase, and optionally a hydrotrope to form a dual-phase mouthwash or a dual-phase mouthwash composition. In a preferred embodiment, the orally acceptable vehicle may include a mixture of water, glycerin, propylene glycol, and/or sorbitol. In at least one embodiment, the orally acceptable vehicle may include water and glycerin.

As discussed above, the oral care composition may include the hydrophilic phase, the hydrophobic phase, and optionally a hydrotrope. The hydrotrope may include compounds that solubilize hydrophobic compounds in aqueous solutions. The hydrotrope may be a low molecular weight amphiphilic compound having a hydrophilic functional group and a low molecular weight hydrophobe. The hydrophobic functional group may attach to an organic moiety of the hydrophobic compounds to facility the solubility thereof in the aqueous solutions. Illustrative hydrotropes of the oral care composition and the dual-phase mouthwash may include, but are not limited to, aromatic sulfonates, aromatic phosphate esters, glycerin, di and polycarboxylates, polyglycols, and alcohols, including polyhydric alcohols.

Fluoride Ion Source

The oral care composition may further include one or more fluoride ion sources (e.g., soluble fluoride salts). A wide variety of fluoride ion-yielding materials may be employed as sources of soluble fluoride. Examples of suitable fluoride ion-yielding materials may be found in U.S. Pat. No. 3,535,421 to Briner et al., U.S. Pat. No. 4,885,155 to Parran, Jr. et al., and U.S. Pat. No. 3,678,154 to Widder et al., the disclosures of which are incorporated herein by reference. Illustrative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In a preferred embodiment, the fluoride ion source includes sodium fluoride. The amount of the fluoride ion source in the oral care composition may be less than 0.080 wt %, less than 0.07 wt %, less than 0.060 wt %, less than 0.050 wt %, less than 0.040 wt %, less than 0.030 wt %, or less than 0.025 wt %. For example, the amount of the fluoride ion source may be about 0.0220 wt %. In another embodiment, the fluoride ion source is present in an amount to provide a total of about 100 to about 20,000 ppm, about 200 to about 5,000 ppm, or about 500 to about 2,500 ppm, fluoride ions.

Flavoring Agents

The oral care composition may also include one or more flavoring agents. Illustrative flavoring agents may include, but are not limited to, sweeteners, essential oils and various flavoring aldehydes, esters, alcohols, and the like. The flavoring agents may also include, but are not limited to, sucralose, dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof (e.g., sodium saccharin), dipeptide-based intense sweeteners, cyclamates, dihydrochalcones and mixtures thereof. Examples of the essential oils include oils of spearmint, peppermint, wintergreen, sassafras, clove, sage, eucalyptus, marjoram, cinnamon, lemon, lime, grapefruit, and orange. In another example, the flavoring agents may include menthol, carvone, and anethole. In a preferred embodiment, the flavoring agent includes peppermint and spearmint. In a more preferred embodiment, the flavoring agent includes a Firmenich Newman Flavor. The amount of the flavoring agent in the oral care composition may be less than 0.35 wt %, less than 0.30 wt %, less than 0.25 wt %, or less than 0.20 wt %. For example, the amount of the flavoring agent in the oral care composition may be about 0.0 wt % to about 0.30 wt %, about 0.05 wt % to about 0.25 wt %, about 0.10 wt % to about 0.20 wt %. In a preferred embodiment, the amount of the flavoring agent in the oral care composition is about 0.10 wt % to about 0.20 wt %.

Chelating and Anti-Calculus Agents

The oral care composition may optionally include one or more chelating agents and/or one or more anti-plaque agents. The chelating agents may be capable or configured to form complexes or bind with calcium found in cell walls of bacteria to weaken the cell walls and enhance or augment bacterial lysis. Illustrative chelating and anti-calculus agents may include, but are not limited to, phosphates and polyphosphates (e.g., pyrophosphates), polyaminopropanesulfonic acid (AMPS), hexametaphosphate salts, zinc citrate trihydrate, polypeptides, polyolefin sulfonates, polyolefin phosphates, and diphosphonates. Illustrative chelating and anti-calculus agents may also include soluble pyrophosphates salts. In a preferred embodiment, the pyrophosphate salts of the oral care composition may be or include an alkali metal pyrophosphate salt. Illustrative alkali metal pyrophosphate salts include tetra alkali metal pyrophosphate, dialkali metal diacid pyrophosphate, trialkali metal monoacid pyrophosphate, and mixtures thereof, where the alkali metals are sodium or potassium. For example, in a preferred embodiment, the alkali metal pyrophosphate salts may be or include tetrasodium pyrophosphate and/or tetrapotassium pyrophosphate. The alkali metal pyrophosphate salts may be in either a hydrated form or a non-hydrated form.

The chelating or anti-plaque agents may be present in the oral care composition in an effective amount. For example, an effective amount of the pyrophosphate salt may generally be an amount that provides at least 0.5 wt % of the pyrophosphate ions in the oral care composition. In another example, an effective amount of the pyrophosphate salt may generally be an amount that provides at about 0.9 wt % to about 3.0 wt % of the pyrophosphate ions in the oral care composition. In yet another example, an effective amount of the pyrophosphate salt may generally be an amount that provides at about 0.30 wt % to about 1.40 wt % of the pyrophosphate ions in the oral care composition. The amount of the chelating or anti-plaque agents in the oral care composition may be from about 0.30 wt %, about 0.35 wt %, about 0.40 wt %, about 0.45 wt %, about 0.50 wt %, about 0.55 wt %, or about 0.60 wt % to about 0.90 wt %, about 0.95 wt %, about 1.00 wt %, about 1.05 wt %, about 1.10 wt %, about 1.15 wt %, about 1.20 wt %, about 1.25 wt %, about 1.30 wt %, about 1.35 wt %, or about 1.40 wt %. In an exemplary embodiment, the oral care composition is free or substantially free of the chelating or anti-plaque agents. For example, the oral care composition is free or substantially free of tetrasodium pyrophosphate and/or tetrapotassium pyrophosphate.

Anti-Plaque Agents

The oral care composition may optionally include one or more anti-plaque (e.g., plaque disrupting) agents. Any orally acceptable anti-plaque agent may be used. Illustrative anti-plaque agents may include, but are not limited to, stannous salts, copper salts, magnesium salts, strontium salts, zinc salts, dimethicone copolyols (e.g., cetyl dimethicone copolyol), papain, glucoamylase, glucose oxidase, urea, calcium lactate, calcium glycerophosphate, strontium polyacrylates, and mixtures thereof.

Water

The oral care composition may include water. The water used in the oral care composition may be deionized and free of organic impurities. Water may make up the balance of the oral care composition after all other components are included. For example, the amount of water in the oral care composition may be from about 10 wt % to 90 wt %, about 40 wt % to about 85 wt %, or about 60 wt % to about 80 wt %. In another example, the amount of water in the oral care composition may be at least 60 wt %, at least 65 wt %, at least 70 wt %, at least 75 wt %, at least 76 wt %, or at least 78 wt %. In a preferred embodiment, the amount of water in the oral care composition may be about 75 wt % to about 77 wt %. The amount of water in the oral care composition may include free water added and water introduced with other components or materials of the oral care composition. For example, the amount of the water in the oral care composition may include free water and water associated with humectants, flavoring agents, or any other component of the oral care composition.

Humectants

The oral care composition (e.g., the hydrophilic phase thereof) may include humectants. The humectants may be capable or configured to reduce evaporation and lower water activity. It should be appreciated that the humectants may also be capable of imparting desirable sweetness or flavor to the oral care composition. Illustrative humectants may include, but are not limited to polyhydric alcohols, such as glycerin, sorbitol, xylitol, propylene glycol, as well as other polyols, and mixtures thereof.

Surfactants

The oral care composition may include one or more surfactants. For example, the oral care composition may include one or more anionic surfactants, one or more cationic surfactants, one or more zwitterionic surfactants, one or more nonionic surfactants, and mixtures thereof. Examples of suitable surfactants may be found in U.S. Pat. No. 3,959,458 to Agricola et al., U.S. Pat. No. 3,937,807 to Haefele, and U.S. Pat. No. 4,051,234 to Gieske et al., the disclosures of which are incorporated herein by reference.

In at least one embodiment, the oral care composition includes at least one anionic surfactant. Illustrative anionic surfactants may include, but are not limited to, water-soluble salts of higher fatty acid monoglyceride monosulfates, such as a sodium salt of a monosulfated monoglyceride of hydrogenated coconut oil fatty acids, such as sodium N-methyl N-cocoyl taurate, sodium cocomonoglyceride sulfate. Illustrative anionic surfactants may also include higher alkyl sulfates. As used herein, "higher alkyl" refers to $C_{6-30}$ alkyl. For example, in a preferred embodiment the anionic surfactant is sodium lauryl sulfate. The anionic surfactants may also include higher alkyl-ether sulfates. For example, the anionic surfactants may have a formula $CH_3(CH_2)_mCH_2(OCH_2CH_2)_nOSO_3X$, where m is 6-16, n is 1-6, and X is Na or K. In an exemplary embodiment, m is 10, and n is 2, 3, or 4, and X is Na or K. For example, the anionic surfactant may be sodium laureth-2 sulfate $(CH_3(CH_2)_{10}CH_2(OCH_2CH_2)_2OSO_3Na)$. In another embodiment, the anionic surfactant may include higher alkyl aryl sulfonates, such as sodium dodecyl benzene sulfonate (sodium lauryl benzene sulfonate), and higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate. In an exemplary embodiment, the anionic surfactant is a water soluble salt of alkyl sulfates having from 10 to 18 carbon atoms in the alkyl radical and water soluble salts of sulfonated monoglycerides of fatty acids having from 10 to 18 carbon atoms. For example, the anionic surfactant may be or include, sodium lauryl sulfate, sodium lauroyl sarcosinate, sodium coconut monoglyceride sulfonates, or the like, and mixtures thereof.

In at least one embodiment, the oral care composition may also include at least one nonionic surfactant. Accordingly, the oral care composition may include at least one anionic surfactant, at least one nonionic surfactant, or both an anionic surfactant and a nonionic surfactant. The nonionic surfactant may function as an emulsifier. Illustrative nonionic surfactants may include, but are not limited to, poloxamers or the like. For example, the nonionic surfactants may include polysorbate 20, poloxamer 407, poloxamer 338, or the like, and mixtures thereof. The nonionic surfactants may also include, but are not limited to, ethoxylated and hydrogenated ethoxylated castor oils, such as those commonly designated as PEG NN castor oil or PEG NN hydrogenated castor oil, where "NN" designates the number of ethylene oxide units polymerized onto the castor oil to form the nonionic surfactant. For example, the nonionic surfactants may be or include PEG 16, 20, 25, 30, 40, 50, 60, 80, 100, 200, and combinations thereof. In a preferred embodiment, the nonionic surfactant is PEG 40 hydrogenated castor oil, which is commercially available as CREMOPHOR® RH40 from BASF Corp. of Florham Park, N.J.

The amount of any one or more of the surfactants in the oral care composition may be from about 0.010 wt %, about 0.020 wt %, about 0.030 wt %, about 0.040 wt %, about 0.045 wt %, about 0.049 wt %, or about 0.050 wt % to about 0.051 wt %, about 0.055 wt %, about 0.060 wt %, about 0.065 wt %, about 0.070 wt %, about 0.075 wt %, about 0.080 wt %, or greater. In another example, the amount of any one or more of the surfactants in the oral care composition may be about 0.010 wt % to about 0.090 wt %, about 0.020 wt % to about 0.080 wt %, about 0.030 wt % to about 0.070 wt %, about 0.040 wt % to about 0.060 wt %, about 0.045 wt % to about 0.055 wt %, or about 0.050 wt % to about 0.051 wt %. In yet another example, the amount of any one or more of the surfactants in the oral care composition may be greater than 0.010 wt %, greater than 0.020 wt %, greater than 0.030 wt %, greater than 0.040 wt %, greater than 0.045 wt %, greater than 0.049 wt %, or greater than 0.050 wt %. The amount of any one or more of the surfactants in the oral care composition may also be from about 0.10 wt %, about 0.20 wt %, about 0.30 wt %, about 0.40 wt %, about 0.45 wt %, about 0.49 wt %, or about 0.50 wt % to about 0.51 wt %, about 0.55 wt %, about 0.60 wt %, about 0.65 wt %, about 0.70 wt %, about 0.75 wt %, about 0.80 wt %, or greater. In another example, the amount of any one or more of the surfactants in the oral care composition may be about 0.10 wt % to about 0.90 wt %, about 0.20 wt % to about 0.80 wt %, about 0.30 wt % to about 0.70 wt %, about 0.40 wt % to about 0.60 wt %, about 0.45 wt % to about 0.55 wt %, or about 0.50 wt % to about 0.51 wt %. In yet another example, the amount of any one or more of the surfactants in the oral care composition may be greater than 0.10 wt %, greater than 0.20 wt %, greater than 0.30 wt %, greater than 0.40 wt %, greater than 0.45 wt %, greater than 0.49 wt %, or greater than 0.50 wt %.

In at least one embodiment, the oral care composition includes at least one anionic surfactant and at least one nonionic surfactant. For example, the surfactant in the oral care composition may include sodium lauryl sulfate, poloxamer 407, and poloxamer 338. In a preferred embodiment, the surfactant in the oral care composition includes sodium lauryl sulfate in an amount of about 0.050 wt %, poloxamer 407 in an amount of about 0.50 wt %, poloxamer 338 in an amount of about 0.50 wt %, and PEG-40 hydrogenated castor oil in an amount of about 0.100 wt %. It should be appreciated, however, that the oral care composition may not include the anionic surfactant. For example, the oral care composition may omit at least the sodium lauryl sulfate.

Other Ingredients

The oral care composition may optionally include one or more further ingredients. For example, the oral care composition may include one or more antimicrobial agents and/or one or more preservatives such as, methylisothiazolinone (MIT), sodium benzoate, potassium sorbate, benzyl alcohol, and combinations thereof. In another example, the oral care composition may include one or more antibacterial agents selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, other metal ions (e.g., stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol, and other piperidino derivatives, nicin preparations, chlorite salts; and mixtures of any of the foregoing. In an exemplary embodiment, the antibacterial agent includes cetylpyridinium chloride (CPC).

The oral care composition may optionally include one or more pH modifying agents. For example, the oral care composition may include one or more acidifying agents and/or one or more basifying agents to reduce and/or increase the pH, respectively. The oral care composition may also include one or more buffering agents to control or modulate the pH within a predetermined or desired range. Illustrative buffering agents may include, but are not limited to, sodium bicarbonate, sodium phosphate, sodium hydroxide, sodium carbonate, sodium acid pyrophosphate, citric acid, sodium citrate, and mixtures thereof. Sodium phosphate may include, monosodium phosphate ($NaH_2PO_4$), disodium phosphate ($Na_2HPO_4$), trisodium phosphate ($Na_3PO_4$), and mixtures thereof. In a preferred embodiment, the buffering agent is anhydrous sodium phosphate dibasic or disodium phosphate.

In at least one embodiment, the acidifying, buffering, and/or buffering agents may be included in the oral care composition to provide the oral care composition with a pH between 2 to 10, 2 to 8, 3 to 9, 4 to 8, 6 to 10, or 7 to 9. Additional orally acceptable pH modifying agent may be used, including without limitation carboxylic, phosphoric, and sulfonic acids, acid salts (e.g., monosodium citrate, disodium citrate, monosodium malate, etc.), alkali metal hydroxides, such as sodium hydroxide, carbonates, such as sodium carbonate, bicarbonates, sesquicarbonates, borates, silicates, phosphates (e.g., monosodium phosphate, trisodium phosphate, pyrophosphate salts, etc.), imidazole and mixtures thereof. The one or more pH modifying agents may be optionally present in an amount effective to maintain the oral care composition in an orally acceptable pH range. In a preferred embodiment, the buffering agent includes anhydrous sodium phosphate dibasic or disodium phosphate, and phosphoric acid (e.g., syrupy phosphoric acid; 85%-Food Grade).

Methods

In various embodiments, the present disclosure provides methods to optically brighten or visually whiten the surface of the teeth in a human or animal subject. The method may include contacting the surface of the teeth with the oral care composition of the present disclosure. As used herein "animal subject" includes non-human mammals such as canines, felines, and horses. The oral care composition may be contacted with an oral surface of the human or animal subject to thereby whiten teeth in a highly efficacious manner.

In various embodiments, the oral care composition prepared in accordance with the present disclosure may be applied regularly to an oral surface, for example on a daily basis, at least one time daily for multiple days, or alternately every second or third day. In some embodiments, the oral care composition is applied to the oral surfaces from 1 to 3 times daily, for at least 2 weeks up to 8 weeks, from four months to three years, or more, up to a lifetime.

In some embodiments, the oral care product (e.g., the mouthwash) or the oral care composition thereof may be applied directly to the teeth using a delivery device, such as a pen, (e.g., a COLGATE® whitening pen or a COLGATE® ACTIS™ whitening pen, Colgate-Palmolive Company, New York, N.Y.), a liquid stick having an applicator, such as a felt tip, brush, roller ball, or non-woven pad, sufficient to effect whitening.

In some embodiments, the oral care composition of the present disclosure or the blue dye and/or blue pigment thereof is maintained on the surface of the tooth for a plurality of minutes or hours. In some embodiments, the blue dye and/or blue pigment is maintained on the surface of the teeth for from about 1 minute to about 8 hours. In some embodiments, the blue dye and/or blue pigment is maintained on the surface of the teeth for from about 5 minutes to about 4 hours. In some embodiments, the blue dye and/or blue pigment is maintained on the surface of the teeth for from about 10 minutes to about 120 minutes. In some embodiments, the blue dye and/or blue pigment is maintained on the surface of the teeth for from about 15 minutes to about 60 minutes. In some embodiments, the blue dye and/or blue pigment is maintained on the surface of the teeth for from about 20 minutes to about 45 minutes.

Some embodiments provide a method wherein a delivery device, such as a whitening pen is stored within an oral care implement, such as a toothbrush. In some embodiments, the delivery device, such as a whitening pen is removed from the oral care implement prior to application of the composition to the tooth. In some embodiments, the composition is applied to the tooth after brushing with the oral care implement.

The examples and other embodiments described herein are exemplary and not intended to be limiting in describing the full scope of compositions and methods of this disclosure. Equivalent changes, modifications and variations of specific embodiments, materials, compositions and methods may be made within the scope of the present disclosure, with substantially similar results.

EXAMPLES

Example 1

The equivalence between 0.0014 wt % of CI Food Blue 5 and 0.002 wt % of FD&C Blue No. 1 is demonstrated in Example 1. To demonstrate the equivalence, two mouthwashes (1) and (2) were prepared. Mouthwash (1) included polyphosphates, GANTREZ®, and 0.0014 wt % CI Food Blue 5. Mouthwash (2) included polyphosphates, GANTREZ®, and 0.002 wt % FD&C Blue No. 1. Each of the mouthwashes (1) and (2) were tested in-vitro, and the results of the in-vitro experiments are summarized below in Table 2.

TABLE 2

| Results of In-Vitro Experiments of Mouthwash (1) and (2) | | |
|---|---|---|
| | (1) Polyphosphates & 0.0014 wt % CI Food Blue 5 ($\Delta$WIO) | (2) Polyphosphates & 0.002 wt % FD&C Blue No. 1 ($\Delta$WIO) |
| Initial Treatment (0 min soak in saliva) | 8.6 | 8.5 |
| 10 min soak in saliva | 2.1 | 1.7 |
| 30 min soak in saliva | 1.6 | 1.2 |

As is evident in Table 2, mouthwash (1) having about 0.0014 wt % of CI Food Blue 5 is equivalent to mouthwash (2) having about 0.002 wt % FD&C Blue No. 1, as the in-vitro experiments indicated that substantially the same amount of instant whitening efficacy ($\Delta$WIO) was achieved with these respective levels of blue dyes. It should further be noted that 0.0014 wt % of CI Food Blue 5 is the molar equivalent to 0.002 wt % FD&C Blue No. 1 in the mouthwashes.

Example 2

Two mouthwashes were prepared, including a control mouthwash (3) and a test mouthwash (4). The control mouthwash (3) was prepared by combining 0.0014 wt % of CI Food Blue 5 and GANTREZ® Polymer, and the test mouthwash (4) was prepared by combining 0.002 wt % of FD&C Blue No. 1 and a phosphate/acrylate co-polymer. As demonstrated in Example 1, about 0.0014 wt % of CI Food Blue 5 is equivalent to about 0.002 wt % FD&C Blue No. 1. The test mouthwash (4) was prepared by combining the ingredients/components according to Table 3. The ingredients/components in the control mouthwash (3) differs from the test mouthwash (4) in that the control mouthwash (3) uses 0.0014 wt % of CI Food Blue 5, which is the molar equivalent of 0.002 wt % of FD&C Blue No. 1, as included in the test mouthwash (4). The control mouthwash (3) also contains a stain prevention system including GANTREZ® Polymer, phosphates, and zinc. The test mouthwash (4) contains a single stain prevention system including sodium acrylates/methacryloylethyl phosphate copolymer. The respective stain prevention systems in each of the control mouthwash (3) and the test mouthwash (4) represent the formula differences influencing the whitening systems.

TABLE 3

Composition of Test Mouthwash (4)

| Ingredient | (Wt. %) |
|---|---|
| Water | 76.28190 |
| Flavoring Agent | 0.282000 |
| Fluoride Ion Source | 0.050 |
| Preservatives | 0.050000 |
| Nonionic Surfactants | 1.10000 |
| FD&C Blue No. 1 | 0.002000 |
| Buffering Agents | 0..712000 |
| Sorbitol - Non-Crystal 70% Soln. | 5.500000 |
| Glycerin; 99.0%-101.0% | 7.500000 |
| Propylene Glycol | 7.00000 |
| Sodium Acrylates/Methacryloylethyl Phosphate Copolymer | 1.500000 |
| Anionic Surfactants | 0.050000 |
| Total | 100.000 |

Each of the mouthwashes (3) and (4) were tested on a set of 16 human teeth. It is noted that the same set of teeth was used for each of the mouthwashes (3) and (4) to minimize experimental variability. Accordingly, prior to each testing cycle, the set of the teeth was brushed with a silica toothpaste for 10 minutes, and a baseline or reference color was measured with a spectrophotometer. In each testing cycle, the set of teeth was soaked in saliva for 15 minutes in an aluminum tray. The set of teeth was then treated with one of the mouthwashes (3) and (4) by gently pouring the saliva out of the tray and off of the teeth, and adding 10 mL of the respective mouthwash (3) and (4) to the tray. The tray containing the respective mouthwash (3) and (4) was then gently agitated to mimic or model the act of swishing. After one minute, the respective mouthwash (3) and (4) was poured out of the tray, and the set of teeth was rinsed with 100 mL of water. The CieLab values were then measured with a spectrophotometer and the WIO value was calculated as discussed above. The spectrophotometer was also used to measure the color following a 10 min soak in saliva and a 30 min soak in saliva, and the whitening efficacy (ΔWIO) was calculated as discussed above. The results of the whitening efficacy (ΔWIO) are summarized below in Table 4.

TABLE 4

ΔWIO of Mouthwashes

| | (3) Control Mouthwash (GANTREZ® Polymer) (ΔWIO) | (4) Test Mouthwash (Phosphate/acrylate Copolymer) (ΔWIO) |
|---|---|---|
| Initial Treatment (0 min soak in saliva) | 7.3 | 7.9 |
| 10 min soak in saliva | −0.4 | 4.4 |
| 30 min soak in saliva | 0.9 | 3.3 |

As is evident from Table 4, the test mouthwash (4), including the phosphate/acrylate copolymer, had a greater initial whitening efficacy (ΔWIO=7.9) than the control mouthwash (3) (ΔWIO=7.3); and thus, exhibited a visually perceived color closer to white. Accordingly, when the phosphate/acrylate copolymer is included in the oral care composition, the teeth exhibit increased retention of the blue dye on the surface or enamel thereof, thereby resulting in relatively increased whitening efficacy (ΔWIO) as compared to the control (3) or commercially available mouthwash, which included the GANTREZ® Polymer. As is further evident from Table 4, the test mouthwash (4) incorporating the phosphate/acrylate polymer exhibited an increased whitening effect upon extended exposure to saliva over time, as compared to the control mouthwash (3).

Accordingly, it has been surprisingly and unexpectedly discovered that when the phosphate/acrylate polymer and the blue dye of the oral care composition are combined with one another, the oral care composition exhibits a synergistic effect and provides a significant and unexpected increase in whitening efficacy and duration over conventional mouthwashes without the phosphate/acrylate copolymer. It has also been surprisingly and unexpectedly discovered that when the phosphate/acrylate polymer and the blue dye of the oral care composition are combined with one another, the oral care composition exhibits a synergistic effect and provides a significant and unexpected increase in whitening efficacy and duration over commercially available oral care compositions that include a blue dye and/or blue pigment and a synthetic anionic linear polycarboxylate, such as GANTREZ®.

The present disclosure has been described with reference to exemplary embodiments. Although a limited number of embodiments have been shown and described, it will be appreciated by those skilled in the art that changes may be made in these embodiments without departing from the principles and spirit of the preceding detailed description. It is intended that the present disclosure be construed as including all such modifications and alterations insofar as they come within the scope of the appended claims or the equivalents thereof.

What is claimed is:
1. An oral care composition, comprising:
   an orally acceptable vehicle;
   a blue dye and/or a blue pigment having a blue to blue-violet color with a hue angle in the CIELAB system from about 200 to about 320 degrees; and
   a phosphate/acrylate copolymer.
2. The oral care composition of claim 1, wherein the phosphate/acrylate copolymer is a copolymer of a mixture of acrylic acid, methacrylic acid, and 2-hydroxyethyl meth- acrylate phosphate, wherein the 2-hydroxyethyl methacrylate phosphate has the chemical formula:

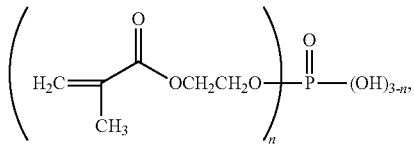

wherein n is 0, 1, or 2.

3. The oral care composition of claim 2, wherein the mixture comprises the acrylic acid in a molar percentage of 70-90%, the methacrylic acid in a molar percentage of 5-20%, and the 2-hydroxyethyl methacrylate phosphates in a molar percentage of 1-10%.

4. The oral care composition according to claim 2, wherein:
the acrylic acid is present in a molar percentage of about 80% to about 90%, optionally about 85%;
the methacrylic acid is present in a molar percentage of about 5% to about 15%, optionally about 11%; and
the 2-hydroxyethyl methacrylate phosphates is present in a molar percentage of about 2% to about 6%, optionally about 4%.

5. The oral care composition according to claim 1, wherein the phosphate/acrylate copolymer has a weight average molecular weight of about 10 kDa to about 500 kDa, optionally about 10 kDa to about 200 kDa, further optionally about 10 kDa to about 40 kDa.

6. The oral care composition according to claim 1, wherein the oral care composition comprises about 0.70 wt % to about 2.20 wt %, optionally about 0.90 wt % to about 2.00 wt %, further optionally about 1.00 wt % to about 1.95 wt %, of the phosphate/acrylate copolymer.

7. The oral care composition according to claim 1, wherein the phosphate/acrylate copolymer is a sodium salt of a sodium acrylates/methacryloylethyl phosphate copolymer.

8. The oral care composition according to claim 1, wherein the oral care composition is a mouthwash.

9. The oral care composition according to claim 1, wherein the oral care composition comprises about 0.0010 wt % to about 0.0030 wt %, optionally about 0.0015 wt % to about 0.0025 wt %, further optionally about 0.002 wt % of the blue dye and/or the blue pigment.

10. The oral care composition according to claim 1, wherein the blue dye and/or the blue pigment comprises a dye, optionally the dye comprises FD&C Blue No. 1.

11. The oral care composition according to claim 1, further comprising a fluoride ion source, optionally the fluoride ion source comprises sodium fluoride.

12. The oral care composition according to claim 1, further comprising an antibacterial agent.

13. The oral care composition according to claim 1, wherein the oral care composition is free of peroxides.

14. The oral care composition according to claim 1, further comprising at least one anionic surfactant and at least one nonionic surfactant, optionally the anionic surfactant comprises sodium lauryl sulfate.

15. A method for whitening teeth, comprising contacting the oral care composition of claim 1 with a surface of the teeth.

* * * * *